(12) United States Patent
Rue et al.

(10) Patent No.: US 7,850,639 B2
(45) Date of Patent: *Dec. 14, 2010

(54) IMPLANTATION DEVICE FOR SUBCUTANEOUS IMPLANTATION OF AN OBJECT UNDER THE SKIN

(75) Inventors: Matthew L. Rue, Flemington, NJ (US); David S. Tierney, Cranbury, NJ (US)

(73) Assignee: Endo Pharmaceuticals Solutions, Inc., Chadds Ford, PA (US)

( * ) Notice: Subject to any disclaimer, the term of this patent is extended or adjusted under 35 U.S.C. 154(b) by 9 days.

This patent is subject to a terminal disclaimer.

(21) Appl. No.: 12/415,681

(22) Filed: Mar. 31, 2009

(65) Prior Publication Data

US 2009/0247939 A1 Oct. 1, 2009

Related U.S. Application Data

(63) Continuation of application No. 11/531,311, filed on Sep. 13, 2006, now Pat. No. 7,510,549, which is a continuation of application No. 10/406,397, filed on Apr. 3, 2003, now Pat. No. 7,214,206.

(51) Int. Cl.
*A61M 31/00* (2006.01)
*A61M 5/178* (2006.01)
*A61M 1/30* (2006.01)

(52) U.S. Cl. .............. 604/19; 604/57; 604/59
(58) Field of Classification Search .......... 604/19, 604/36, 38, 57–64, 93.01, 116, 117, 158, 604/164.01; 606/116, 117
See application file for complete search history.

(56) References Cited

U.S. PATENT DOCUMENTS

| 4,661,103 | A | 4/1987 | Harman |
| 7,214,206 | B2 * | 5/2007 | Rue et al. .............. 604/19 |

FOREIGN PATENT DOCUMENTS

WO WO-99/33512 7/1999

OTHER PUBLICATIONS

Notice of Reasons for Refusal in JP Appl. No. 2006-509680 (English translation and Japanese document included), transmitted Oct. 20, 2009; received Nov. 16, 2009. (Patents listed in the Notice were previously cited in IDS filed Aug. 7, 2009.).

* cited by examiner

*Primary Examiner*—Matthew F Desanto
(74) *Attorney, Agent, or Firm*—Gilberto M. Villacorta; Jeffrey R. Lomprey; Foley & Lardner LLP

(57) ABSTRACT

A device for inserting implantable objects beneath the skin of a patient includes a handle for grasping the device and a base connected to the handle. The base comprises a post, a cannula, and a flexible actuator positioned in an angled track. The cannula is positioned coaxially around and is longitudinally slidable over the post from an extended position, where an implantable object is retained in the cannula, to a retracted position, where the implantable object is released from the cannula. A flexible actuator positioned on an angled track in the base is slidably engaged with a boss on the cannula and is used to move the cannula from an extended position to a retracted position to release the implantable object from the cannula; the actuator flexes between a locked and an unlocked position. The angled track provides for control of the release of the implantable object.

13 Claims, 6 Drawing Sheets

IMPLANTATION DEVICE FOR SUBCUTANEOUS IMPLANTATION OF AN OBJECT UNDER THE SKIN

CROSS REFERENCE TO RELATED APPLICATIONS

This application is a continuation of U.S. patent application Ser. No. 11/531,311, now U.S. Pat. No. 7,510,549, filed on Sep. 13, 2006, which in turn is a continuation of U.S. patent application Ser. No. 10/406,397, now U.S. Pat. No. 7,214,206, filed on Apr. 3, 2003, the contents of which are both incorporated herein by reference for any and all purposes.

FIELD OF THE INVENTION

The present invention relates generally to an implanting device and a method for inserting implantable objects beneath the skin of a patient. More particularly, the present invention relates to an implanting device which provides improved control of implantable object release due to an angled track located on the base of the implanting device.

BACKGROUND

Drugs may be delivered to patients by a variety of methods including oral intravenous administration, inhalation of aerosols, an epidermal patch, and subcutaneous implants. The method chosen depends, among other things, upon the desired therapeutic concentration of the drug or pharmaceutical to be achieved in the patient and the duration the concentration must be maintained.

Recently released materials and pharmaceuticals have been developed which allow a drug to be subcutaneously introduced or administered beneath the skin of a patient so that the drug is slowly released over a long period of time. Such implants allow a drug to be dispensed in a relatively uniform dose over many months or years. This method of administering drugs is becoming especially important and popular as a method of administering contraceptives.

Previously, subcutaneous implants and other types of implants have been inserted beneath the skin by use of a trocar system, which is a two piece system including a cannula and an obdurator. First, an incision is made through the skin and the cannula and obdurator are inserted together through the skin. Next, the obdurator is withdrawn, leaving the cannula in place as a guide for inserting the implant. The implant is inserted through the cannula, and the obdurator is used to push the implant to the end of the cannula. The obdurator is then used to force the implant out of the cannula while the cannula is withdrawn, such that the implant is deposited in the channel previously occupied by the cannula. The cannula and obdurator are then withdrawn completely, leaving the implant in place beneath the skin.

This trocar insertion process requires substantial expertise in coordinating the pressing of the obdurator and the withdrawing of the cannula to deposit the implant in the channel. If these two processes are not properly coordinated, the implant may be forced into the tissue so that the implant has to make its own channel as it is inserted. Forcing the implant into the tissue causes additional trauma to the tissue and may cause the implant to become damaged by the force exerted by the obdurator. This is especially true for a hydrogel implant. While subcutaneous implantation may be done surgically using a scalpel to make the incision and a trocar system to plane the implant, such methods require a physician or other highly trained person. Recently improved instruments for inserting subcutaneous implants have been developed which typically require far less skill to operate, and thus may be better suited for non-surgical physicians and other less skilled individuals, and require less time to perform the implantation procedure.

U.S. Pat. No. 4,105,030 discloses an implanting apparatus for use in subcutaneously implanting multiple pellets in animals. The apparatus provides a one-handed implanting system that reduces the risk of trauma from forcing the implant into the tissue, and it also reduces contamination. The animal implant apparatus includes a handle, a needle containing the pellets to be implanted, and a rod positioned within the needle for pushing the pellets out of the needle. Once the needle containing the pellets has been inserted subcutaneously, a spring loaded trigger on the handle is activated which causes the needle to be automatically withdrawn by a spring leaving the implanted pellets in place. However, the handle configuration of this implanting device is designed for use in animals, such as cattle, and due to its size and shape, it would be difficult to use for inserting implants subcutaneously in humans. Further, it is not possible to control the motion of the needle in this device because the needle will automatically retract upon activation of the trigger. The complex spring loaded propelling system and trigger of this implant apparatus increase the chances that the device will jam and fail to eject the pellets when required.

Contraceptive steroids that are implanted subcutaneously are normally imbedded in biologically inert polymers, some of which are biodegradable. The pellets made from such materials are typically long and cylindrical in cross section, and the size of these materials is on the order of the size of a pencil lead. The materials are generally flexible, ranging from somewhat flexible to very flexible nature. See, for example, U.S. Pat. No. 4,451,253, which describes some exemplary contraceptive pellets and an apparatus for individually implanting such pellets subcutaneously.

The size and shape of an implant pellet are important in determining the rate of delivery of a particular drug from a subcutaneous implant. Practical consideration put constraints on the dimensions of a subcutaneous implant. In particular, the length of an implant is generally limited. A typical implant is on the order of 1 ½ to 2 inches long. Longer implants are much more difficult to accurately locate. They are also more susceptible to breakage, which may affect the drug delivery rate and, in general, are simply more cumbersome and cosmetically apparent. Because of this, it is frequently necessary to implant a desired amount of a drug as a plurality of individual, shorter implant pellets rather than as a single longer pellet. Thus, an instrument which can quickly allow a physician or nurse to implant a plurality of pellets with minimal physical and psychological trauma to a patient would be desirable. When implanting several implants, care must be taken to accurately place the implants in a manner such that one does not interface with the dissolution of the others.

SUMMARY

Embodiments of the present invention include a device which may be used for implanting various pharmaceuticals and therapeutic drug delivery devices. Such implantable objects may include those such as silicone rubber capsules or tubes that contain a synthetic progestin birth control hormone. The flexible tubes may steadily release a low dose of hormone into the bloodstream.

One embodiment of the present invention is an implant device for inserting implantable objects subcutaneously into a patient, comprising a handle for grasping the device during insertion of an implantable object and a base connected to the handle. The base comprises a post, a cannula, and a flexible actuator positioned in an angled track. The cannula is positioned coaxially around and is longitudinally slidable over the post from an extended position, where an implantable object is retained in the cannula, to a retracted position, where the implantable object is released from the cannula. A flexible actuator positioned on an angled track in the base is slidably engaged with a boss on the cannula and is used to move the cannula from an extended position to a retracted position to release the implantable object from the cannula; the actuator flexes between a locked and an unlocked position.

The flexible actuator of the implant device may be locked to prevent movement of the cannula and thereby prevents any undesired dispensing or insertion of implantable objects. By pressing the flexible actuator into a second position (when the actuator is in the track in a distal position with respect to the handle) a locking portion of the actuator is engaged to prevent retraction of the cannula. The lock may be released by alternately pressing the flexible actuator to a first position.

The implanting device may further include one or more implantable objects within the cannula. The implanting device may also include a cartridge for holding multiple implantable objects that are sequentially fed into the cannula after an implantable object is dispensed by movement of the actuator and cannula. The cartridge may be removably mounted and have a channel containing an implantable object that is parallel to a central bore of the cannula.

According to a further aspect of the present invention, a method of inserting a subcutaneous implantable object with an implanting device of the present invention includes inserting a cannula of the implanting device beneath the skin of a patient with an implantable object positioned within the cannula and manually retracting the cannula along the angled track using the flexible actuator to release the implantable object beneath the skin. The implanting device may then be withdrawn from the patient or another implantable object from a cartridge positioned within the cannula may be subsequently inserted. The implanting device used in the method includes a handle, a base, and a cannula slidably engaged with a flexible actuator located in an angled track.

According to another further aspect of the present invention, a kit for inserting an implantable object and maintaining sterile conditions includes an implanting device including a handle and a base connected to the handle, the base comprising a post, a cannula, and a flexible actuator positioned in an angled track, where the cannula is positioned coaxially around and is longitudinally slidable over the post from an extended position, where an implantable object is retained in the cannula, to a retracted position, where the implantable object is released from the cannula, and where the actuator is positioned on an angled track in the base is slidably engaged with a boss on the cannula and is used to move the cannula from an extended position to a retracted position to release the implantable object from the cannula; a cutting device for making an implanting incision in a patient's tissue; supplies for maintaining sterility of the implant insertion process; and wound dressings.

The implantable object and implanting device of the present invention may be useful for insertion of implants coated with a sol-gel coatings or with hydrogel implants. The active agent may be slowly released by the implant or the coating on the implant when placed in watery environments such as blood or tissue. The device may be used to implant any such implant.

The present invention provides embodiments of an implanting device for inserting implantable objects which provides improved control of implantable object release due to the angled track located on the base of the implanting device. The flexible actuator is positioned on the angled track, which helps to prevent the forcing of the implantable object into the tissue, as such uncontrollable forcing can cause trauma to the tissue and may cause the implant to become damaged.

DESCRIPTION OF THE DRAWINGS

In part, other aspects, features, benefits and advantages of the embodiments of the present invention will be apparent with regard to the following description, appended claims and accompanying drawings where:

DETAILED DESCRIPTION

Figure 1:
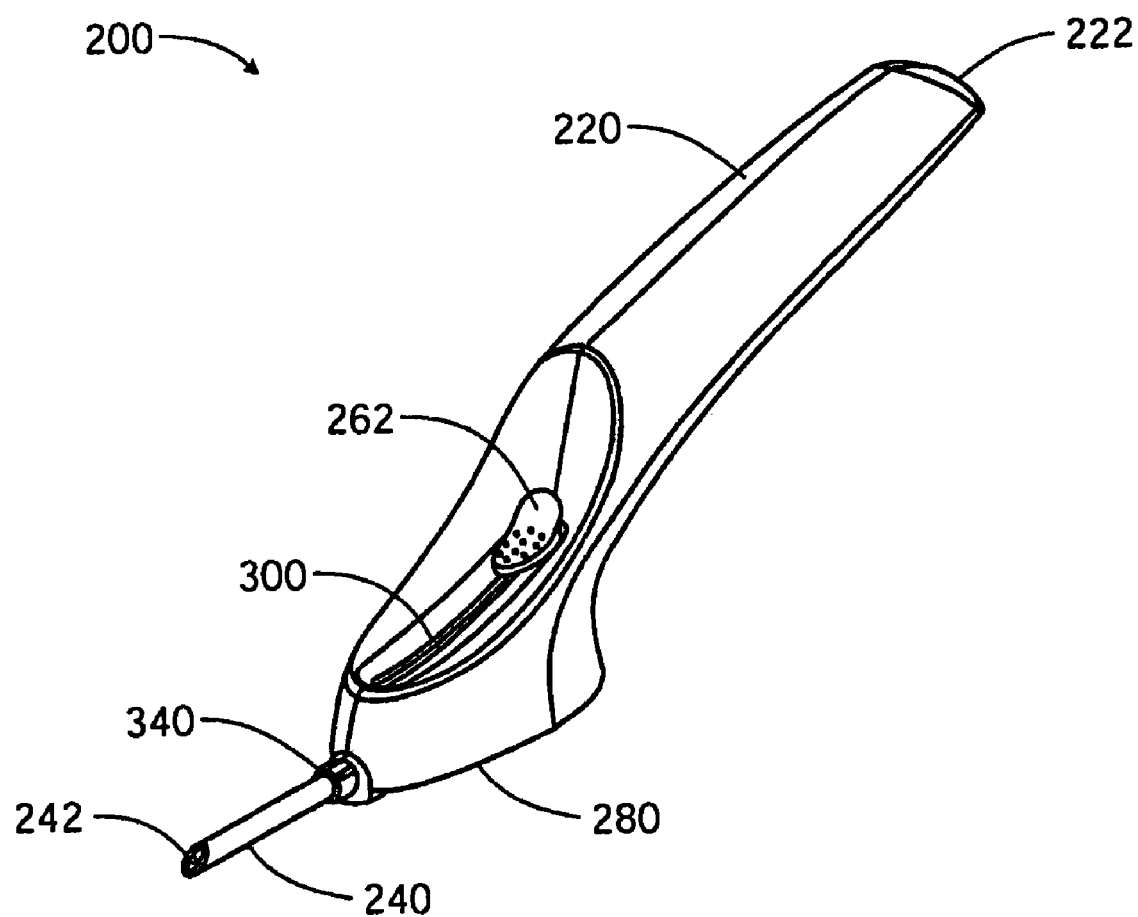
FIG. 1 is an isometric view of an implanting device according to the present invention with the cannula retracted and the flexible actuator is in an unlocked position.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The present invention provides an implanting device for subcutaneously inserting implantable objects containing beneficial agents, such as pharmaceuticals for the prevention, treatment, and diagnosis of disease. The implanting device 200 according to one embodiment of the present invention is illustrated in the perspective view in FIG. 1. The implanting device 200 includes a handle 220, a movable elongated cannula 240 (shown in a retracted position), a flexible actuator button 262 connected to a flexible actuator 260 (shown in FIG. 3) for moving the cannula 240 along a post rod 244 (shown in FIG. 3), and a base 280. The base 280 is distal to the handle end 222. In the retracted position, the cannula 240 is drawn into the interior of the handle base 280 by the flexible actuator button 262 as it is moved or slid toward the handle end. The flexible actuator button 262 is guided by an angled track 300 which is non-parallel with respect to the axis of motion of the cannula 240 or the axis of the post rod 244 (shown in FIG. 3). The cannula 240 may be slid or moved with respect to the post rod 244 (shown in FIG. 3) and housing base 280 with cannula guide 340. Movement of the flexible actuator 260 in a direction toward the cannula guide 340 and along the track 300 away from the handle 220 results in extension of the cannula 240 through the cannula guide 340.

Figure 2:
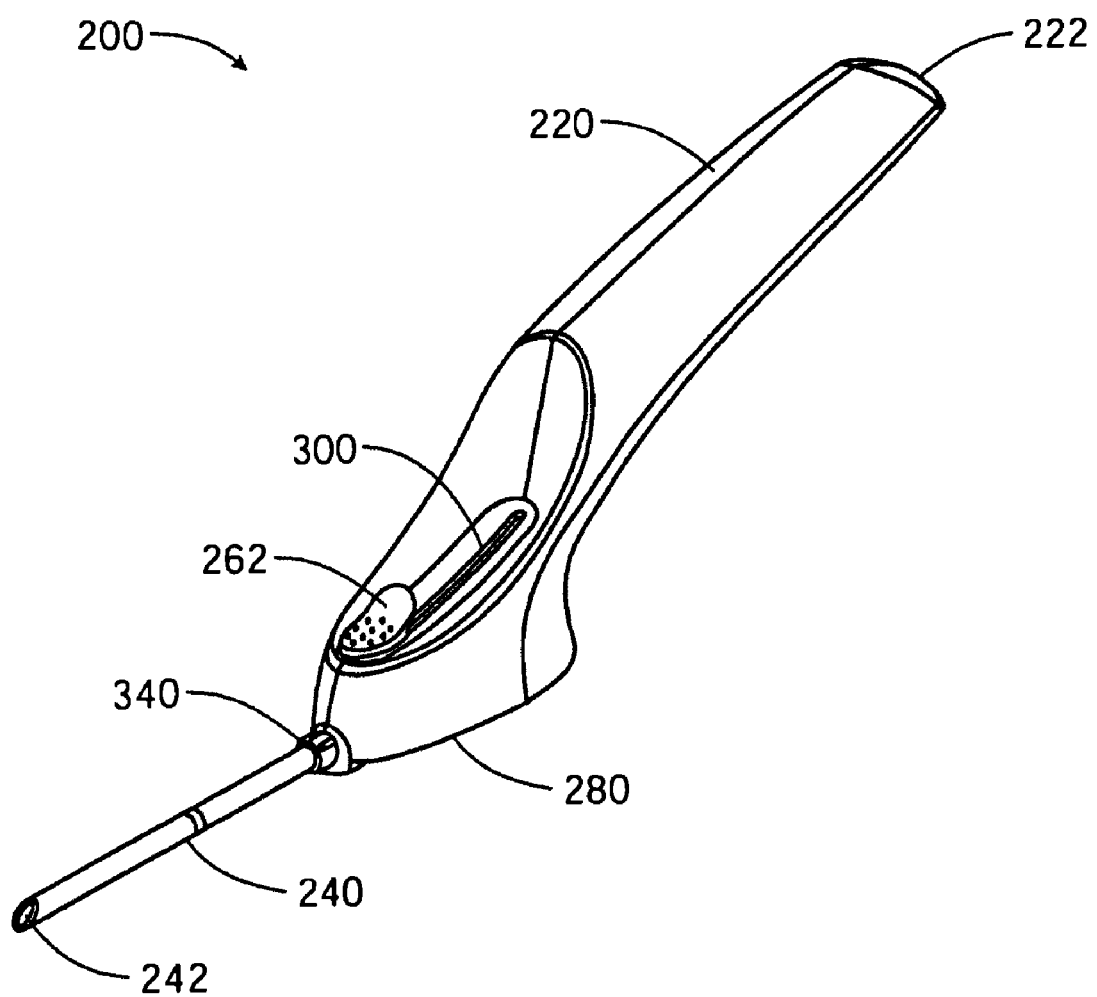
FIG. 2 is an isometric view of the implanting device with the cannula in a fully extended position with the flexible actuator in a locked position.

In FIG. 2 the implanting device 200 is shown with the cannula 240 in an extended position. In FIG. 2 the flexible actuator button 262 is shown distal to the handle end 222. In this position the flexible actuator may be locked to prevent withdrawal of the cannula 240 and unintended insertion of implantable objects. Movement of the flexible actuator button 262 in a direction away from the cannula guide 340 and along the angled track 300 towards the handle 220 causes retraction of the cannula 240 and release of an implantable object (not shown) positioned within the bore 242 of the cannula.

Motion of the flexible actuator is along an angled ramp which provides increased precision in control of the movement of the cannula along the post rod axis. This provides the user with the advantage of greater control of insertion of implantable objects.

Figure 3:
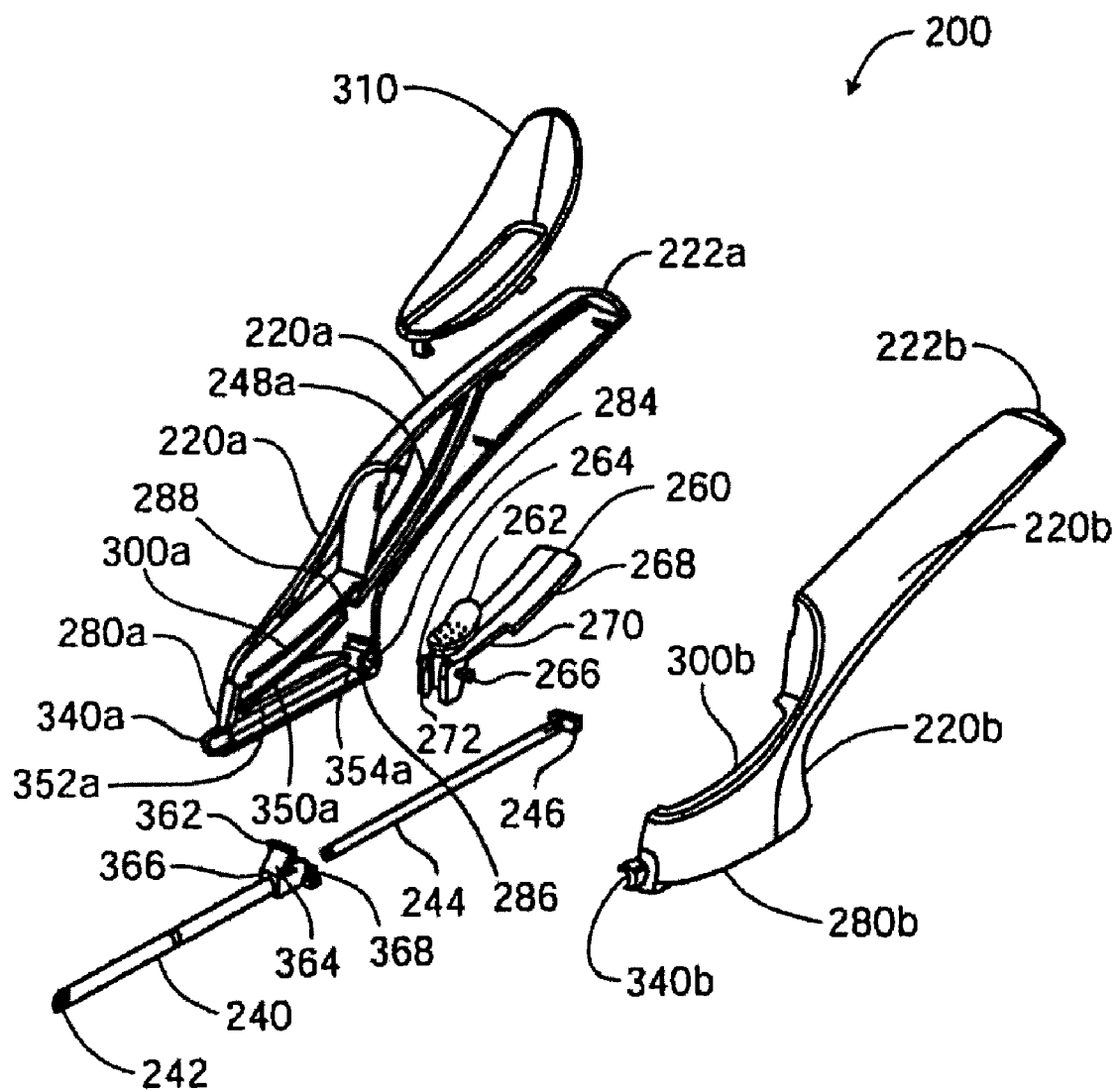
FIGS. 3 and 3A are an exploded view of an implanting device according to an embodiment of the present invention.
Figure 3A:
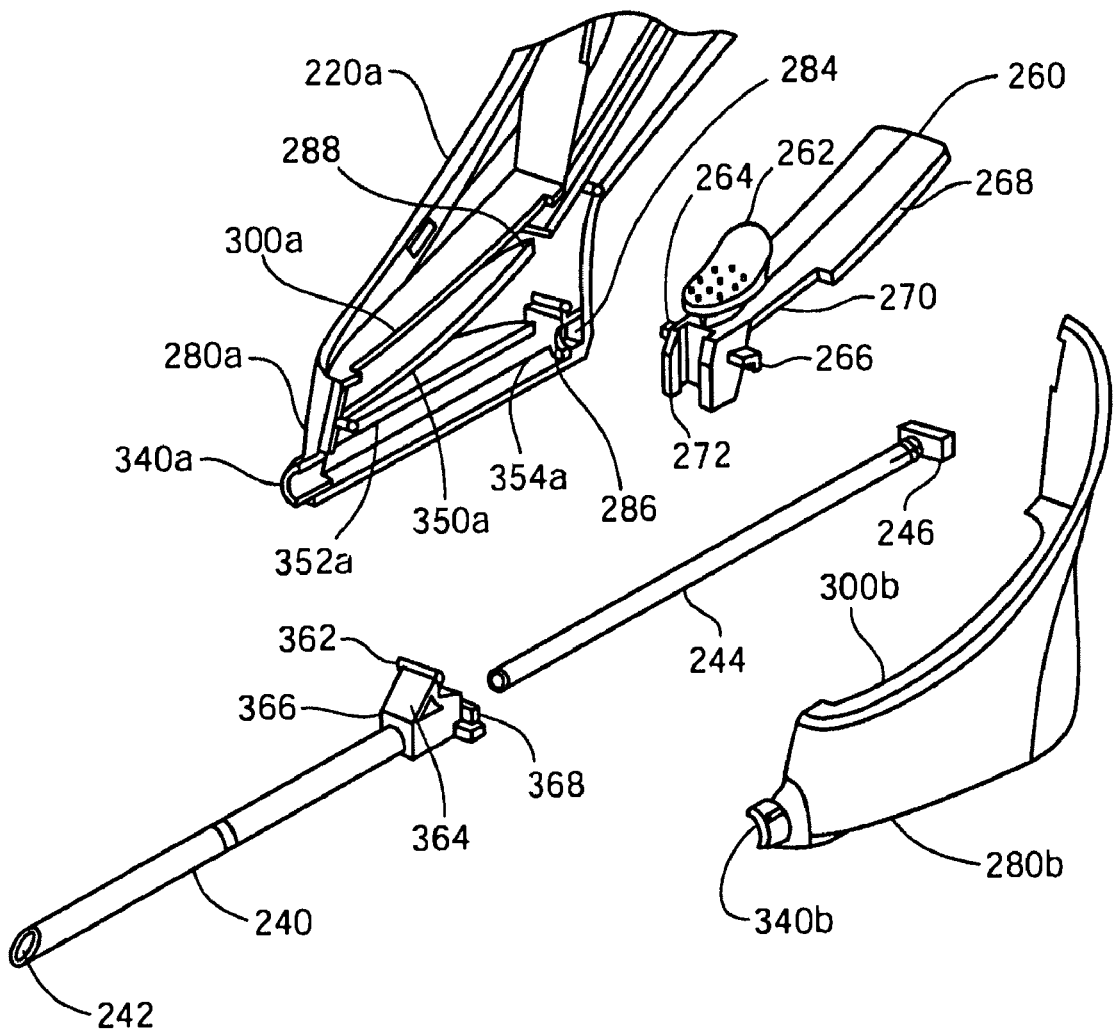

With respect to FIG. 3 there is shown an exploded isometric view of the embodiment shown in FIGS. 1 and 2. In this Figure, the implanting device 200 is shown in two portions 200a and 200b, which includes a handle 220 having first and second portions 220a and 220b, a base 280 having first and second portions 280a and 280b; a cannula guide 340 having first and second cannula guide portions 340a and 340b; and a handle end 222 including handle end portions 222a and 222b. The angled track 300 is formed from two opposing recessed track walls 300a and 300b which, when the portions 200a and 200b of the implanting device are assembled, form the angled track 300. Within the implanter handle 220 are portions of a flexible actuator channel 248a, (and 248b in handle 220b not shown in FIG. 3), which, when assembled, form a flexible actuator channel 248 for guiding the tab 268 of the flexible actuator within the assembled implanter handle 220.

The flexible actuator 260 in FIG. 3 includes a button 262, a boss channel 272, a lower guide post 264 (not shown in FIG. 3), lower guide post 266, thin profile guide 270, and tab 268. The button 260 is seated in the scoop 310. The boss channel 272 receives the guide posts 362 and 364 from the cannula boss 360. Movement of the flexible actuator 260 along the angled track 300, in the direction away from the cannula guide 340 and toward the post boss retainer 248, allows cannula boss guide posts 362 and 364 within the boss channel 272 to remain at a constant position relative to the post 244, while the boss channel 272 moves relative to them and at the same time pulls the cannula 240 toward the post retainer 248. The boss channel 272 engages the cannula boss guide posts 362 and 364 and permits a pulling or pushing force to be exerted on the cannula 240, for extension and retraction, as the flexible actuator 260 is moved along the angled track 300.

Flexible actuator guide post 266 and flexible actuator guide post 264 (now shown in FIG. 3) are attached to flexible actuator 260 and rest on top of angled guide ramp 350b (not shown in FIG. 1C) and angled guide ramp 350a respectively. An angled guide ramp 350 is formed by joining guide ramp portion 350a shown in FIG. 3 and guide ramp portion 350b (not shown in FIG. 3) together. The flexible actuator guide posts 264 (not shown in FIG. 3) and 266 shown in FIG. 3 move parallel to the angled guide ramp 350b (not shown in FIG. 3) and angled guide ramp 350b respectively translating movement of the flexible actuator 260 along the angled track 300 into movement of the boss channel 272 perpendicular to the axis of the cannula 240 as the flexible actuator 260 is moved toward or away from the post retainer 248. Cannula boss guide posts 366 (not shown in FIG. 3) and 368 lie below linear guide 352a and 352b (not shown in FIG. 1C) and on top of base step 354a and 354b (not shown in FIG. 3) maintains the cannula in a substantially fixed orientation with respect to the base 280.

The degree to which movement of the flexible actuator 260 between any two points along the guide ramp 350 is translated into linear motion of the cannula 242 along the post 244 depends upon the angle of the base guide ramp 350. The greater the angle that the base guide 350 makes with respect to the post 244, the more control that may be exerted over lateral movement of the cannula 240. The shape of the base guide ramp portions 350a in FIGS. 3 and 350b (not shown in FIG. 3) may be a linear or curvilinear.

Post 244 is coaxially located within cannula bore 242 and is secured to the housing base 280 by post retainer 248 through post boss 246. The post 244 is inserted into the end of the cannula 242 where the cannula boss 360 is located and protrudes through cannula guide 340 which provides support and alignment for the post 244. The diameter of the cannula guide 340 is made so that movement of the cannula 260 into and out of the base 280 along the post 244 occurs without binding or restriction of the cannula 240 with the inner diameter of the cannula guide 340. The diameter of the cannula guide 340 may also be sized so that it prevents entrainment of fluids, particles, and other debris adhering to the cannula 240 from being drawn into the implanter base 280.

Figure 4:
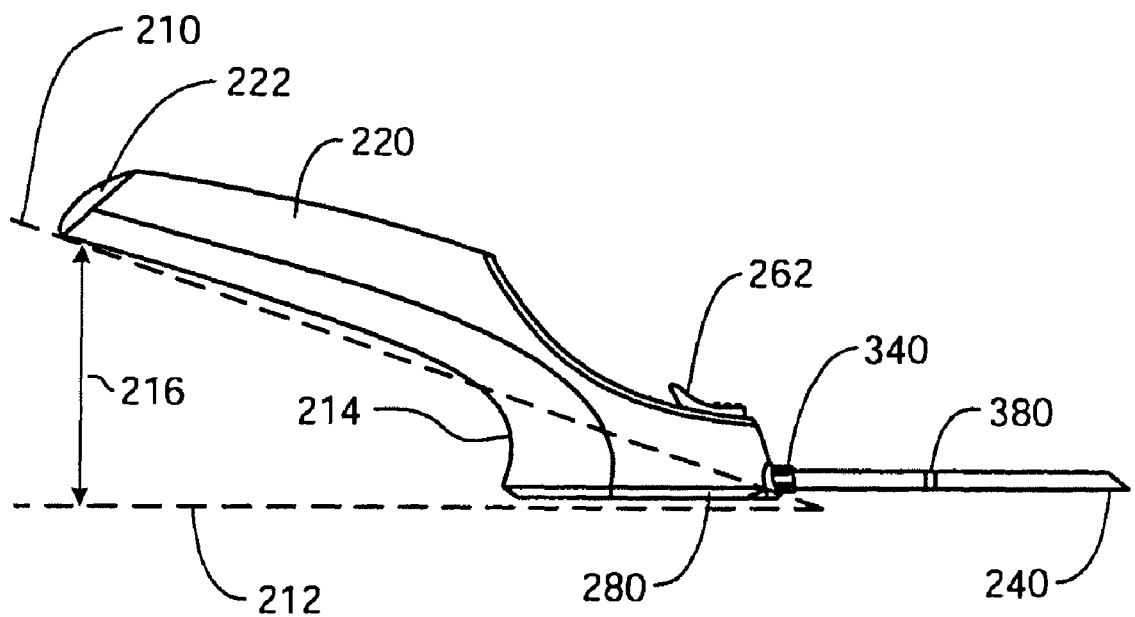
FIG. 4 is a side view of an implanting device according to the present invention with the cannula in a fully extended position with the flexible actuator in a locked position.

FIG. 4 shows a side view of the implanting device of the present invention with the cannula in an extended position. In FIG. 4, the flexible actuator button 262 is shown distal to the handle end 222. In this position, the flexible actuator may be locked to prevent withdrawal of the cannula 240 and unintended insertion of implantable objects. Movement of the flexible actuator button 262 in a direction away from the cannula guide 340 and along the angled track 300 towards the handle 220 causes retraction of the cannula 240 and release of an implantable object (not shown) positioned within the bore 242 of the cannula 240.

Figure 5:
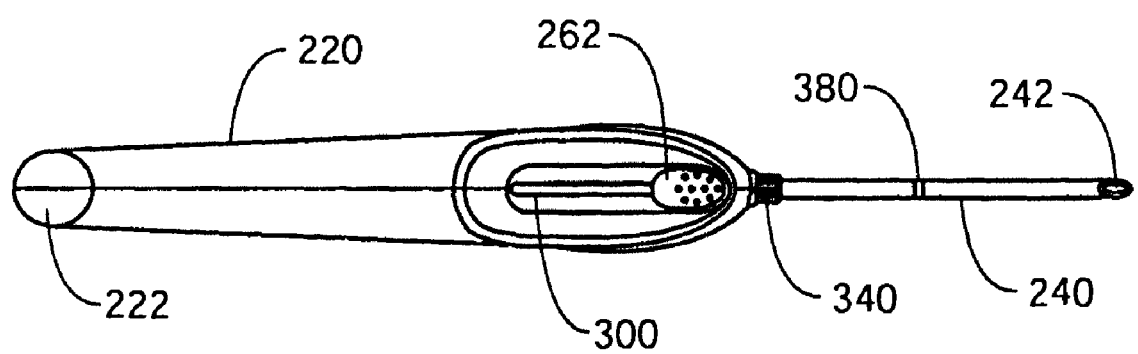
FIG. 5 is a top view of an implanting device according to the present invention with the cannula in a fully extended position with the flexible actuator in a locked position.

FIG. 5 shows a top view of the implanting device of the present invention with the cannula 240 in an extended position. In FIG. 5, the flexible actuator button 262 is shown distal to the handle end 222. In this position, the flexible actuator may be locked to prevent the withdrawal of the cannula 240 and unintended insertion of implantable objects. Movement of the flexible actuator button 262 in a direction away from the cannula guide 340 and along the angled track 300 towards the handle 220 causes retraction of the cannula 240 and release of an implantable object (now shown) position within the bore 242 of the cannula 240.

The implanting device may be made from molded, cast, machined components or combinations of these. For example the implanter portions 200a and 200b may be molded from chemically and mechanically suitable plastics such a polyvinylidine fluoride (PVDF) or ultrahigh molecular weight polyethylene (UPE). The cannula 240 may be made from a variety of surgically acceptable stainless steels or titanium alloys, and the post may be made using similar materials or plastics like PVDF.

The implanter handle 220 includes a grasping position and may fit into the palm of the users hand. The handle is substantially symmetrical so that the implanting device can be used by either right or left handed users. Extending from the handle is a base portion 280 which includes a track 300 in which a flexible actuator 260 slides to extend or retract the cannula 240. The track is formed by two opposed track side walls 300a and 300b angled with respect to the device post 244, and that form a slot extending through the track 300 along a length of the track to receive the actuator 260 and thin profile guide 272.

The cannula 240 includes a boss fitting at an end proximal to the handle 220 of the device. The cannula boss 360 is secured around the proximal end of the cannula 240 and provides guide posts 264 and 266 that fit into a channel on the flexible actuator 260. The cannula boss 360 may be attached to the cannula 240 in any known manner such as by insert molding, press fitting, adhesive bonding, threading, ultrasonic staking, and the like.

The flexible actuator 260 includes a channel which receives the cannula boss guide posts 362 and 364 and allows them to slide and move within the channel. The flexible actuator 260 has a thin profile guide 270 which extends through the slot in the track 300 and guides the flexible actuator 260 in the track 300 as it slides longitudinally along the track. The thin profile guide 270 of the flexible actuator is connected to an actuator button 262 for engagement by a user's finger to move the actuator along the angled track 300. The actuator button 262 may have a ridged, grooved, or knurled slip surface which may be engaged by the user's thumb.

A longitudinal axis passes through a center of the cannula 240 and the post 244 in the base of the implanting device. The track along which the flexible actuator 260 moves is not parallel to this axis along one or more portions of the track; the track may be linear or curvilinear. The track has a distal position which provides a stop for the flexible actuator and also permits securing of the flexible actuator which locks the cannula in the initial loaded position and prevents unintended release of the implantable object from the device. The flexible actuator 260 is released from the locked position by pressing the flexible actuator button 262. When the flexible actuator 260 is in the locked position a substantial force may be applied longitudinally on the distal end of the cannula 240 without causing the cannula to retract.

Once the flexible actuator 260 has been unlocked, further manual pressure on the actuator button 262 in the direction toward the handle 220 causes the flexible actuator to slide along the track. As the actuator slides in the direction of the handle, the cannula 240 is withdrawn over the post 244 and one or more implantable objects held stationary by the post 244 may be released from the cannula 240. The flexible actuator 260 allows the user to manually control the motion of the cannula 260 throughout the implant insertion process. The angle or slope of the track with respect to the axis of the post permits the user to exert greater control over the motion of the cannula than could be achieved using a linear track to guide the withdrawal of the cannula.

Although the implanting device is preferably a single user device, the implanting device according to the present invention may also be made for reuse. The reusable embodiment of the implanting device will preferably be formed of an autoclavable material known to those skilled in the art for sterilization and reuse.

The post 244 is positioned within the base 280 and is fixed within the proximal end of the base by a post retainer 248. The post has a protrusion or boss at one of its ends which engages and secures the post 244 to the post retainer 248. The post retainer 248 is secured to an interior surface of the implanter base. The distal end of the post 244 is configured to engage the implantable object as the cannula 240 is retracted over the post 244. This distal end of the post 244 may have a flat leading edge for engaging the implantable object or may also take on other configuration depending on the particular implantable object to be inserted. Some other distal end configuration include but are not limited to blunt, beveled, concave, and convex end surfaces.

The post 244 preferably has an outer diameter which is somewhat smaller than an inner diameter of the cannula 240 to provide clearance through the cannula tube and limit binding or restriction of the post within the cannula. The post diameter with respect to the cannula should limit the amount of material that can bypass the cannula and become entrapped within the base.

The handle of the present invention is designed for one handed operation with the handle grasped by the hand while the thumb is used to slide the flexible actuator in the angled track. The handle preferably has a size and shape that can be easily manipulated during implant insertion. The orientation of the handle relative to the cannula allows the user to firmly grip the handle, yet easily keep the handle parallel to the skin surface to prevent the cannula from diving into other tissue of piercing out through the skin during insertion. The implanting device includes a bottom surface of the base which is substantially planar and parallel to the cannula.

A distal tip of the cannula 240 may be formed at various beveled angles, such as between about 30 degrees and about 45 degrees, or at a sharp point, such as 27 degrees which can cut skin. The preferred design of the cannula tip is a design with a beveled tip which does not cut unbroken skin and does not require special sharps disposal. The cannula of the implanting device is preferably inserted into the patient through a small incision made in the patient's skin to minimize scaring.

In operation the implanting device may be loaded with an implantable object either manually or with a cartridge. An incision is made at an implantation site and the cannula is inserted through the incision to a desired depth. Preferably, a depth indicating marker, such as a ring, is provided on the cannula to assist in locating the implantable object at a particular depth. Once the cannula is placed under the skin at a desired location for the implantable object, the flexible actuator is drawn back manually causing the cannula to be withdrawn over the implantable object and the post. When the cannula has been fully withdrawn, the implanting device is withdrawn from the patient leaving the implantable object in place.

The two handle portions and base portions may be assembled in any known manner such as by ultrasonic welding, adhesive bonding, press-fit bosses, or a snap fit. A rear surface of the handle rests against the palm of the user to steady the implanting device as the thumb moves the flexible actuator along the angled track. Pressure may also applied to the base by the index finger of the user during insertion of the cannula.

The assembly of the implanting device will be described with reference to the exploded view, which illustrates the implanting device prior to assembly. A cannula 240 with boss 360 secured to it is slid over a post 244 and the flexible actuator 260 is slid onto the upper cannula boss guide posts. This subassembly is oriented in one portion of an implanting device so that the proximal end of the post 244 is secured to a post boss retainer 248. Next, the flexible actuator 260 may be received within the actuator channel, the lower cannula boss guide post is positioned below the linear guide within the base, and the cannula 240 with the post 244 inside of it is received into a cannula guide portion. Placement of the second implanter portion over the first implanter portion with the previously described subassembly positioned inside of it, traps the cannula, its guide posts, and the flexible actuator and its guide posts between cutouts in the second portion of the implanter.

When the implanting device is assembled, the flexible actuator 260 is slidably connected to the upper cannula boss guide posts mounted to the cannula 240. The flexible actuator 260 slides along the angled or curvilinear track 300 from a distal portion of the track which serves as a locking position to the proximal end of the track.

One embodiment of the present invention is a kit which may include additional parts along with an implanting device which may be combined together to implant therapeutics, pharmaceuticals, or microencapsulated sensors into a patient. The kit may include the implanter in a first compartment. A second compartment may includes a syringe, needles, scalpel, and any other instruments needed. A third compartment may includes gloves, drapes, wound dressings and other procedural supplies for maintaining sterility of the implanting process, as well as an instruction booklet. A fourth compartment may include additional cannula and posts. A cover of the kit may include illustration of the implanting procedure and a clear plastic cover may be placed over the compartments to maintain sterility.

Embodiments of the present invention include a device which may be used for implanting various pharmaceuticals, therapeutic drug delivery devices such as silicone rubber capsules that contain a synthetic progestin birth control hormone, hydrogels, or encapsulated microsensors. The angled guide track of the device permits finer control of the cannula motion during implantation which aids in the proper positioning of implants within the patient. Embodiments of the present invention contain fewer parts than other implant devices.

Although the present invention has been described in considerable detail with reference to certain preferred embodiments thereof, other versions are possible. Therefore the spirit and scope of the appended claims should not be limited to the description and the preferred versions contained within this specification.

What is claimed:

1. A device for implanting at least one object beneath the skin of a patient comprising:
   a handle comprising a distal end, a proximal end, and an angled track;
   a base connected to the handle, the base comprising:
     a post longitudinally fixed to the handle, the post extending from the distal end of the handle;
     a hollow cannula positioned coaxially around and longitudinally slidable over the post from an extended position to a retracted position, the hollow cannula configured to receive at least one implantable object in the extended position and release the at least one implantable object in the retracted position; and
   a flexible actuator slidably engaged to the cannula, the flexible actuator configured to move the cannula from the extended position to the retracted position, and flex between a locked and an unlocked position;
   wherein:
     the flexible actuator comprises a button, a boss channel, at least two guide posts, a guide, and a tab extending upwardly and non-parallel from the guide posts attached to the cannula; and
     the boss channel is configured to engage the guide posts and permit a pulling or pushing force to be exerted on the cannula, for extension or retraction, when the flexible actuator tab is moved by moving the button along the angled track.

2. The device of claim 1, wherein the flexible actuator in the distal position of the angled track is configured to engage a locking portion of the flexible actuator when the flexible actuator is pressed.

3. The device of claim 2, wherein the flexible actuator is configured to release from the locked position when the flexible actuator is pressed.

4. The device of claim 1, further comprising the one or more implantable objects.

5. The device of claim 1, wherein the one or more implantable objects comprise one or more of either therapeutics, pharmaceuticals, or microencapsulated sensors.

6. The device of claim 1, further comprising a cartridge removably mounted and parallel to a central bore of said cannula and a means for moving objects into the cannula for delivery upon retraction of said cannula.

7. The device of claim 1, wherein the angled track comprises two opposing recessed track walls angled with respect to the post.

8. The device of claim 1, wherein the angled track is linear or curvilinear.

9. The device of claim 1, wherein the angled track comprises a stop at the distal portion configured to permit securing of the flexible actuator and lock the cannula in a loaded position.

10. The device of claim 1, wherein the base comprises a bottom surface that is substantially planar and parallel to the cannula.

11. The device of claim 1, wherein the cannula comprises a tip at the distal end comprising at least one beveled angle of between 30 and 45 degrees.

12. The device of claim 1, wherein the cannula comprises a tip at the distal end comprising a sharp point of 27 degrees.

13. The device of claim 1, wherein the cannula comprises a depth indicating marker.

\* \* \* \* \*